(12) United States Patent
Silber

(10) Patent No.: US 7,083,480 B2
(45) Date of Patent: Aug. 1, 2006

(54) DOUBLE CONNECTOR FOR MEDICAL SENSOR

(75) Inventor: Daniel A. Silber, Lexington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/537,790

(22) PCT Filed: Dec. 12, 2003

(86) PCT No.: PCT/IB03/05984

§ 371 (c)(1),
(2), (4) Date: Jun. 6, 2005

(87) PCT Pub. No.: WO2004/057704

PCT Pub. Date: Jul. 8, 2004

(65) Prior Publication Data

US 2006/0068649 A1    Mar. 30, 2006

Related U.S. Application Data

(60) Provisional application No. 60/435,246, filed on Dec. 20, 2002.

(51) Int. Cl.
*H01R 4/48* (2006.01)
*H01R 33/08* (2006.01)
(52) U.S. Cl. .................... 439/835; 439/268
(58) Field of Classification Search ........... 439/268, 439/725, 729, 835, 859, 909
See application file for complete search history.

(56) References Cited

U.S. PATENT DOCUMENTS

| 4,268,101 A | | 5/1981 | Stone |
| 4,285,562 A | * | 8/1981 | Teagno et al. ............. 439/222 |
| 5,277,613 A | * | 1/1994 | Neward ..................... 439/729 |
| 5,295,872 A | | 3/1994 | Christensson |

(Continued)

FOREIGN PATENT DOCUMENTS

EP        1 095 670        5/2001

*Primary Examiner*—James R. Harvey
(74) *Attorney, Agent, or Firm*—Tony Piotrowski

(57) ABSTRACT

A double electrode connector for connecting to medical electrodes preferably in an impedance cardiography system includes a connector housing comprising a base having two holes therein of predetermined diameters arranged at predetermined location in the housing, with a first of the two holes associated with a first connector and a second of the two holes associated with a second connector of the double-electrode connector; a pair of biasing elements arranged along a surface of the housing so that each one of the pair of biasing elements is adapted for biasing against an electrode stud inserted in a respective hole of the two holes in the housing; a cable assembly including a twin wire cable and a bend relief, wherein each one of the pair of metal lugs is connected to one of the first connector and second connector, and the bend relief is arranged in a hole in the base to flexibly connect the twin wire cable to respective metal lugs of the pair of metal lugs. The biasing means may include handles to assist with attaching the double connector to two electrodes with a near-zero insertion force towards a patient.

19 Claims, 3 Drawing Sheets

U.S. PATENT DOCUMENTS

| | | | |
|---|---|---|---|
| 5,562,607 A | * 10/1996 | Gyory | 604/20 |
| 5,685,743 A | * 11/1997 | Schmidt et al. | 439/701 |
| 5,782,892 A | * 7/1998 | Castle et al. | 607/37 |
| 5,895,298 A | * 4/1999 | Faupel et al. | 439/729 |
| 5,944,562 A | 8/1999 | Christensson | |
| 6,032,063 A | * 2/2000 | Hoar et al. | 600/372 |
| 2006/0068649 A1 | * 3/2006 | Silber | 439/835 |

* cited by examiner

DOUBLE CONNECTOR FOR MEDICAL SENSOR

CROSS REFERENCE TO RELATED APPLICATION

This application claims the benefit of U.S. provisional application Ser. No. 60/435,246 filed Dec. 20, 2002, which is incorporated herein by reference.

BACKGROUND OF THE INVENTION

1. Field of Invention

The present invention relates to improved electrical clasp structures for transferring electrical signals to a medical electrode. More particularly, the present invention relates to a double connector for impedance cardiography.

2. Description of the Related Art

Impedance cardiography (ICG) is a medical test to determine the pumping capacity of the heart. ICG is a non-invasive and cost-effective technique for determining stroke volume (SV), cardiac output (CO), and thoracic fluid volume (TFC, or ZO). Impedance cardiography is also referred to as "Non-Invasive Continuous Cardiac Output" (NiCCO), which requires four pairs of electrodes to perform the testing.

In prior art systems, such as, for example the IQ System (Wantagh Incorporated, Bristol, Pa.) an operator places eight ICG electrodes (four sets of two) and three ECG electrodes on the patient. In the case of thoracic electrical bioimpedance, the amount of resistance that an electrical current meets is measured as it travels through the thorax. In such systems, there is one connector per electrode.

Other devices exist in the field of electrocardiography (ECG or EKG) that also have one connector per electrode, such as disclosed in U.S. Pat. Nos. 5,944,562 and 5,295,872, both to Christensson.

To date, there is a double electrode being used for impedance cardiography by CardioDynamics of San Diego, Calif. This cable has eight branches and uses two connectors for each double electrode. However, the use of two connectors for each double electrode still requires eight individual connections to these electrodes.

SUMMARY OF THE INVENTION

The present invention provides a zero-insertion force (ZIF) connector that easily connects a two-conductor cable to a medical electrode or medical sensor having two connections. According to an aspect of the invention, the medical electrode or sensor can be disposable, and may include a snap stud connection so the connector attaches with Zero insertion force onto a stud. According to an aspect of the invention, the zero insertion force permits the connector to be attached to the electrode or sensor after the electrode has been positioned on the patient without discomfort.

According to another aspect of the invention, the connector can be polarized to properly attach to the double electrode. The invention also permits the connections to be made faster (only four instead of eight), and reduces the number of branches. In addition, a double connector prevents the substitution of standard (single) ECG electrodes that would introduce variability in the impedance cardiography test results.

BRIEF DESCRIPTION OF THE DRAWINGS

FIG. 1C is a rear view of the double connector with the cover on.

DETAILED DESCRIPTION OF THE INVENTION

It is understood by persons of ordinary skill in the art that the illustrations and description herein are provided for purposes of explanation, and the claimed invention is not limited to the embodiments shown and described, as an artisan can make variations in the design that lie within the spirit of the invention and the scope of the appended claims.

Figure 1A:
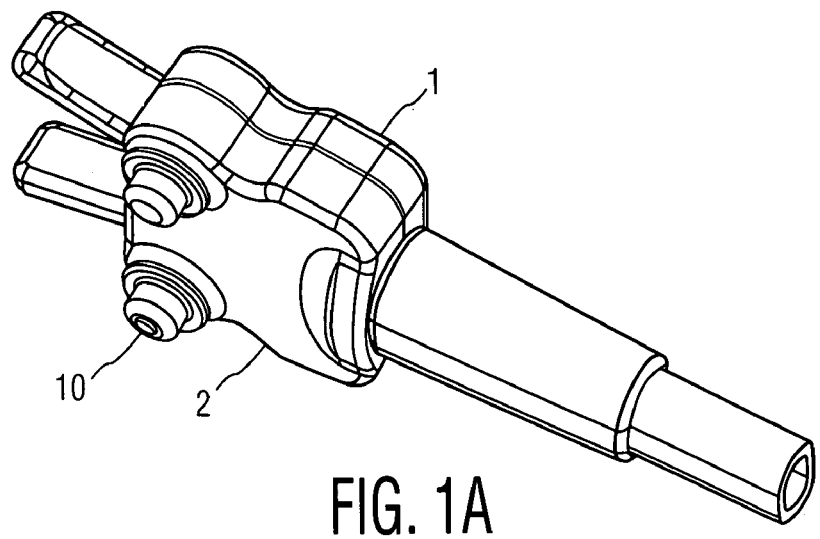
FIG. 1A illustrates a perspective view of a double connector according to the present invention.
Figure 1B:
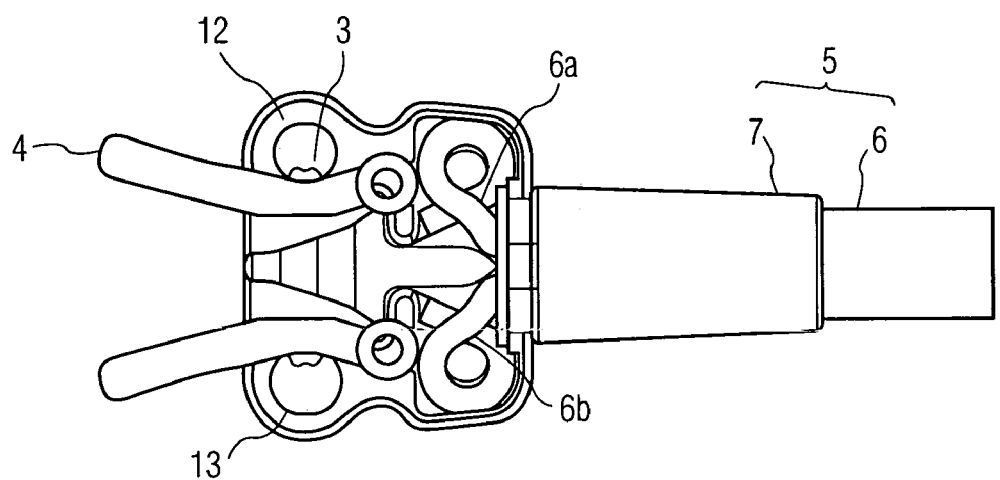
FIG. 1B illustrates another view of the double connector, shown without a cover for more clarity.
Figure 1C:
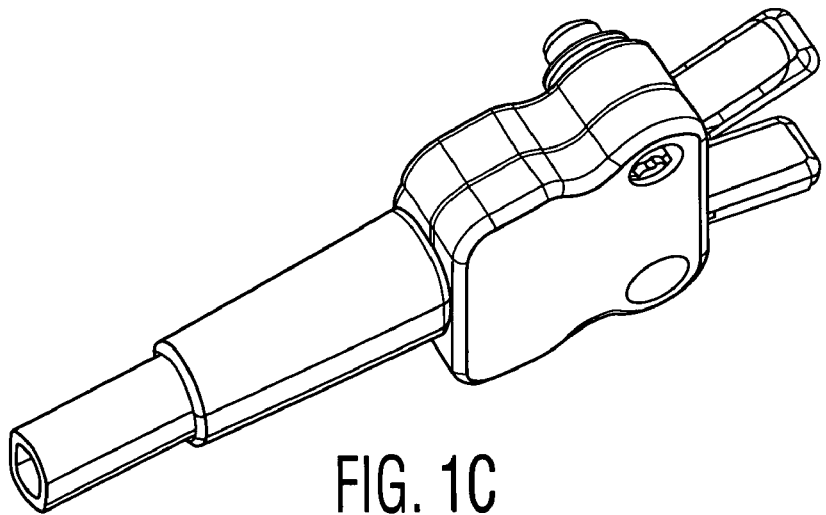

According to an aspect of the invention shown in FIGS. 1A and 1B, a double connector includes a housing comprising a base 1 and cover 2. The base is preferably constructed of injection-molded plastic, but suitable substitutes can be used. The base has two holes 12, 13 (shown in FIG. 1B), with the smaller hole 12 permitting only a smaller stud of a double sensor (Item 15, FIG. 2) to pass but preventing a larger stud (e.g., item 14, FIG. 2) from entering.

Figure 1D:
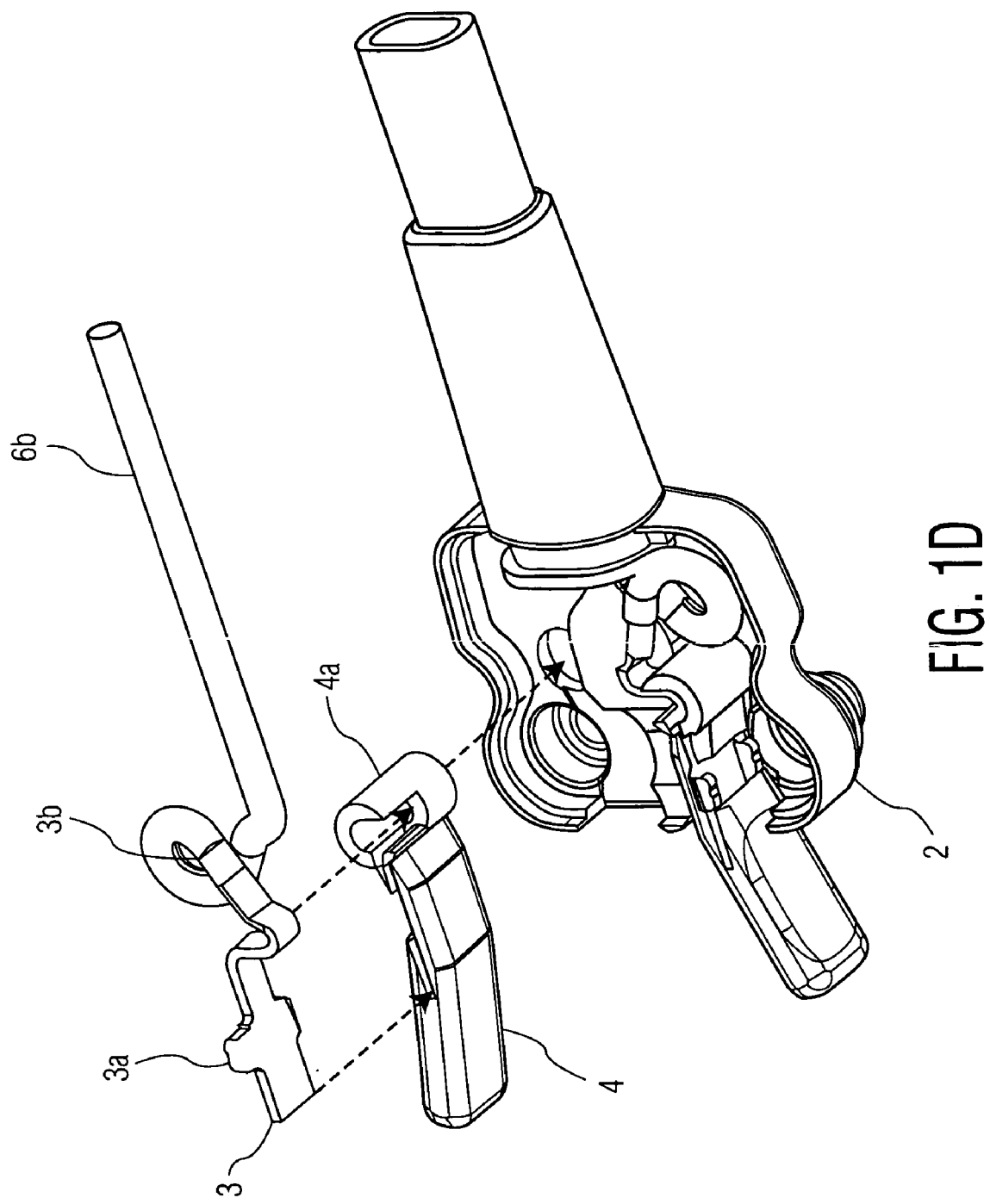
FIG. 1D is an exploded view of some of the components shown in FIGS. 1A and 1B.

As best shown in FIG. 1D, there are two electrical contacts 3 which fit into respective recesses of handles 4. In this particular case, the electrical contacts 3 may serve as leaf springs in and of themselves, but additional contact force can be provided by a coil spring (not shown). The handles 4 have a cylindrical feature 4A at one end, allowing them to rotate within the housing and protrude from the cover 2 at the other end. At least one contact/tab 3A on each spring is positioned to catch the groove of the snap stud 14, 15. The springs may have two tabs, so that a single spring design could be used as either of the two biasing devices. The handles and/or the bend relief can be color coded to facilitate an accurate connection to the electrodes.

As shown in FIG. 1B, a cable assembly 5, which is preferably molded, comprises twin-wire cable 6 (preferably coaxial cable for low noise), and a bend relief 7, which is also preferably molded. The bend relief preferably fits in a hole in the base 1, and should include a flat section to insure proper orientation. The bend relief can be molded in different colors to identify individual connectors.

Prior to final assembly, the conductors of each coaxial wire 6a and 6b are exposed and attached to the respective spring-contact, preferably by crimping into cylindrical feature 3B, but other methods may be used.

The base 1 prevents unwanted motion of the parts and keeps wire strands of one conductor from shorting to the other conductor. It is preferable that the base 1 and cover 2 permanently attach by a snap-fit, adhesive, or ultrasonic weld, although it is possible to make the cover detachable. The cover 2 may optionally include icons to identify proper locations for each connector in the cable harness. Two knobs 10 can be molded onto the cover 2 to simulate the two snap studs of an electrode, allowing one double connector to be attached to another for convenient and neat storage.

In order to install the double connector, an operator squeezes the two handles 4 together, places the connector over the two studs of the electrode, and releases the handles.

A tab 3A on each spring catches in the groove of the respective snap stud of the electrode 13, 14, holding it in place. To remove, the process is reversed. Thus, as the double connector can be connected/disconnected with zero insertion force, there is an advantage in that patient discomfort is reduced as compared to the use of conventional snap studs where there can be bias force applied toward the patient.

Figure 2:
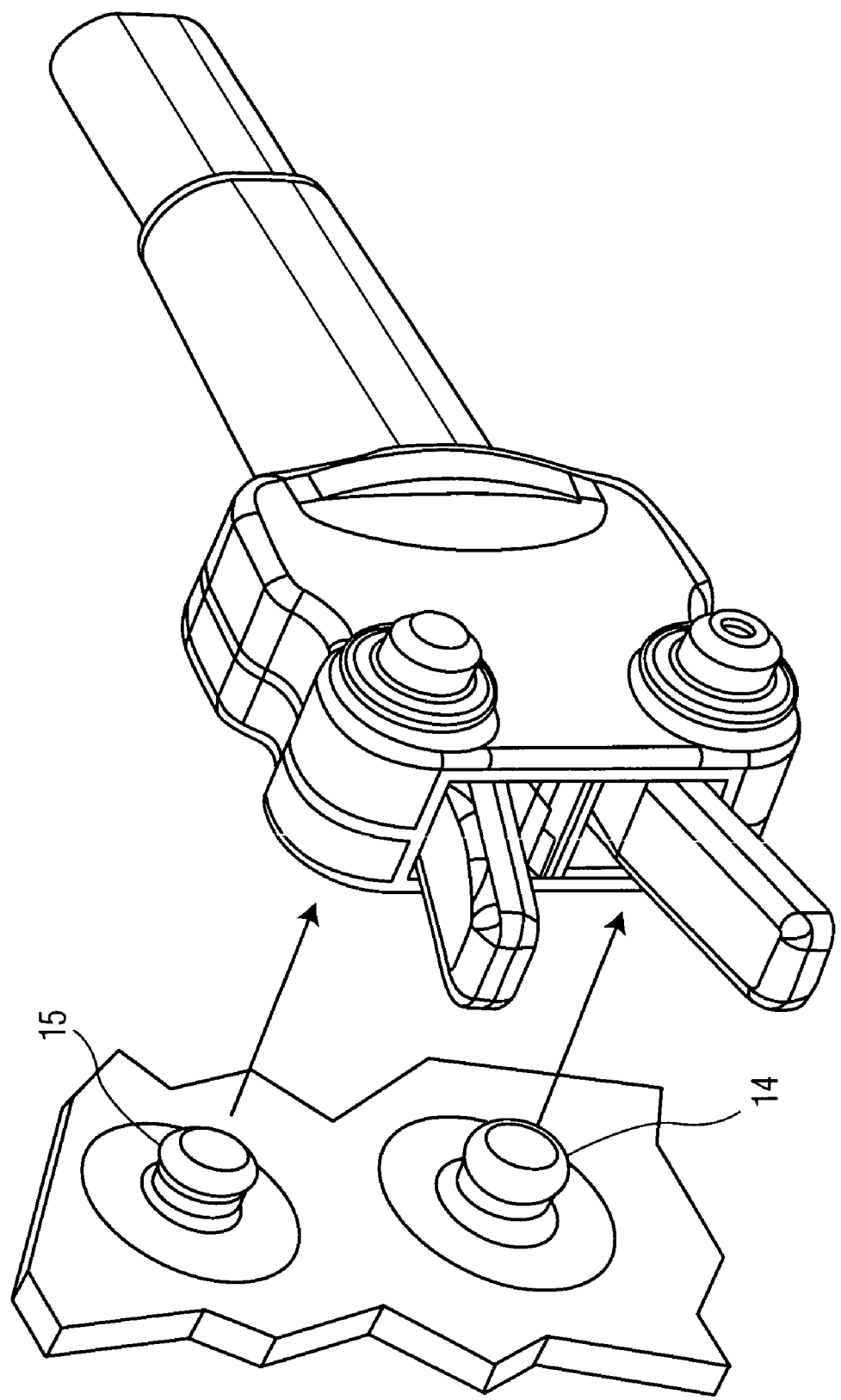
FIG. 2 shows the connector being applied to a medical sensor.

FIG. 2 shows a double connector according to the present invention being applied to the medical sensor. It is to be understood that the proportions are not limitations of the double connector, but are merely included for illustrative purposes.

Some of the many features of the present invention include:

(1) with zero insertion force (meaning the biasing is removable by squeezing the levers), the connector can be attached to the electrode after the double electrode has been positioned on the patient, thereby reducing or eliminating discomfort that would occur with a standard snap fitting or other connector;

(2) the connector can be polarized (by different size holes) to prevent inadvertent interchange of electrodes;

(3) combining two connections in one operation increases the speed with which the connectors can be installed on a patient, and provides more convenience to the practitioner;

(4) reducing the number of branches in the harness from eight to four, reducing the likelihood of tanglement and identification time in prior art devices containing eight branches;

(5) reducing the tendency of capacitance of the two wires to change and create electrical noise by securing the two wires to each other, which would not be possible in a single electrode connector;

(6) a double connector reduces the possibility that standard ECG electrodes would be substituted for (false) economy, so that results would be unnecessarily variable;

(7) the double connector is large enough to have one or more identifying icons arrange thereon;

(8) the design has features that permit color-coding the individual connections;

(9) the design can fit within the electrode profile without overhang, reducing discomfort to the patient from contact by hard edges, and reducing the provider's need to touch the patient's skin; and

(10) self-storage knobs that simulate electrodes permit the connectors to be clipped together when not in use.

There are many modifications that may be made by a person of ordinary skill in the art that would be within the spirit of the invention and the scope of the appended claims. For example, the shape of the housing, the positioning of the holes and/or the shape of the holes to receive the electrodes, and the particular sizes of the elements could be varied according to specific needs. For example, the holes could be slots, ovals, square, polygonal, etc., so long as they properly receive the electrodes. It is also noted that while the double connector is suited for connection with the previously mentioned double-electrodes, it is possible that the connector could also be suited for use with single electrode medical systems.

What is claimed is:

1. A double electrode connector comprising:
a double-electrode connector housing comprising a base having two holes therein of predetermined diameters arranged at predetermined locations in the housing, with a first of the two holes associated with a first connector and a second of the two holes associated with a second connector of the double-electrode connector;
a pair of manually adjustable biasing elements arranged along a surface of the housing so that each one of the pair of biasing elements is adapted for biasing against one of a pair of electrode studs when the studs are inserted in a respective hole of the two holes in the housing; and
a two-wire cable, and a pair of metal contacts, electrically connected to the biasing elements, wherein each one of the pair of metal contacts is coupled to one of a first conductor and second conductor of the two-wire cable.

2. A double electrode connector comprising:
a double-electrode connector housing comprising a base having two holes therein of predetermined diameters arranged at predetermined locations in the housing, with a first of the two holes associated with a first connector and a second of the two holes associated with a second connector of the double-electrode connector;
a pair of biasing elements arranged along a surface of the housing so that each one of the pair of biasing elements is adapted for biasing against one of a pair of electrode studs when the studs are inserted in a respective hole of the two holes in the housing; and
a two-wire cable, and a pair of metal contacts, wherein each one of the pair of metal contacts is coupled to one of a first conductor and second conductor of the two-wire cable,
wherein the first connector and the second connector connect to the respective one of the pair of electrode studs with zero insertion force.

3. The double connector according to claim 1, wherein each of the biasing elements comprises a tab adapted to bias against a respective electrode stud of the pair of electrode studs.

4. A double electrode connector comprising:
a double-electrode connector housing comprising a base having two holes therein of predetermined diameters arranged at predetermined locations in the housing, with a first of the two holes associated with a first connector and a second of the two holes associated with a second connector of the double-electrode connector;
a pair of biasing elements arranged along a surface of the housing so that each one of the pair of biasing elements is adapted for biasing against one of a pair of electrode studs when the studs are inserted in a respective hole of the two holes in the housing; and
a two-wire cable, and a pair of metal contacts, wherein each one of the pair of metal contacts is coupled to one of a first conductor and second conductor of the two-wire cable,
wherein each of the biasing elements comprises a tab adapted to bias against a respective electrode stud of the pair of electrode studs,
wherein the biasing elements comprise leaf springs, and each of the biasing elements further comprises a handle attached to the leaf spring that protrudes out of the connector housing.

5. The double connector according to claim 4, wherein at least one of one the handles and a bend relief is color-coded for connection to specific electrodes.

6. The double connector according to claim 1, wherein the case housing includes a cover and a base, and both are comprised of injection-molded plastic.

7. The double connector according to claim 1, wherein the predetermined diameters of the two holes formed in the base are sized such that one of the two holes is smaller than the other of the two holes.

8. The double connector according to claim 1, wherein the predetermined diameters of the two holes are sized to correspond with a diameter of at least one of the electrode studs.

9. The double connector according to claim 4, wherein each of the biasing elements includes two or more tabs arranged opposite to each other.

10. The double connector according to claim 4, wherein in a first position the handle is arranged so to as to permit an electrode stud to be inserted in one of the two holes in the base.

11. The double connector according to claim 10, wherein in a second position, the handle is arranged so as to bias the leaf spring 3 against the electrode stud inserted in one of the two holes in the base.

12. The double connector according to claim 1, A double electrode connector comprising:
  a double-electrode connector housing comprising a base having two holes therein of predetermined diameters arranged at predetermined locations in the housing, with a first of the two holes associated with a first connector and a second of the two holes associated with a second connector of the double-electrode connector;
  a pair of biasing elements arranged along a surface of the housing so that each one of the pair of biasing elements is adapted for biasing against one of a pair of electrode studs when the studs are inserted in a respective hole of the two holes in the housing; and
  a two-wire cable, and a pair of metal contacts, wherein each one of the pair of metal contacts is coupled to one of a first conductor and second conductor of the two-wire cable,
  further comprising self-storage knobs that protrude in alignment with the two holes in the base to allow attachment to another double connector.

13. The double connector according to claim 1, wherein the connector housing has at least one icon arranged thereon to facilitate a connection with a double electrode.

14. The double connector according to claim 11, wherein the first position of the handle, the leaf spring provides no insertion force downward toward a patient's neck and/or torso.

15. The double connector according to claim 11, wherein in a second position of the handle, the leaf spring provides a biasing force tangential to the neck and/or torso of a patient.

16. The double connector according to claim 4, wherein the housing has two pairs of recesses that each retain an end of one of the respective handles while allowing the handle to pivot.

17. A method of making a double electrode connector, connecting the steps of:
  (a) providing a connector housing comprising a base having two holes therein of predetermined diameters arranged at predetermined locations in the housing, with a first of the two holes associated with a first connector and a second of the two holes associated with a second connector of the double-electrode connector;
  (b) arranging a pair of biasing elements along a surface of the housing so that each one of the pair of biasing elements is adapted for biasing against an electrode stud inserted in a respective hole of the two holes in the housing;
  (c) providing a two wire cable, a pair of metal contacts, and connecting each one of the pair of metal contacts to one of the first conductor wire and second conductor wire, and a bend relief connecting the two wire cable to the housing of the case assembly; and
  (d) providing a manual control for simultaneously biasing the pair of biasing elements away from the electrode studs inserted in the holes.

18. The method according to claim 17, A method of making a double electrode connector, connecting the steps of:
  (a) providing a connector housing comprising a base having two holes therein of predetermined diameters arranged at predetermined locations in the housing, with a first of the two holes associated with a first connector and a second of the two holes associated with a second connector of the double-electrode connector;
  (b) arranging a pair of biasing elements along a surface of the housing so that each one of the pair of biasing elements is adapted for biasing against an electrode stud inserted in a respective hole of the two holes in the housing;
  (c) providing a two wire cable, a pair of metal contacts, and connecting each one of the pair of metal contacts to one of the first conductor wire and second conductor wire, and a bend relief connecting the two wire cable to the housing of the case assembly;
  wherein the first connector and the second connector connect to the electrode studs with zero-insertion-force.

19. The method according to claim 17, wherein the first connector and the second connector connect to the electrode studs by snapping on.

* * * * *